United States Patent
Deacon et al.

[11] Patent Number: 6,162,249
[45] Date of Patent: Dec. 19, 2000

[54] IOI FOR INHIBITING CELL GROWTH AND REDUCING GLARE

[75] Inventors: Jim Deacon, Capistrano Beach; Daniel G. Brady, San Juan Capistrano, both of Calif.

[73] Assignee: Allergan, Irvine, Calif.

[21] Appl. No.: 09/086,882

[22] Filed: May 29, 1998

[51] Int. Cl.$^7$ ........................................ A61F 2/16
[52] U.S. Cl. ............................................. 623/6.16; 623/11
[58] Field of Search ........................................ 623/6, 5, 4

[56] References Cited

U.S. PATENT DOCUMENTS

| | | |
|---|---|---|
| 2,043,840 | 6/1936 | Singer . |
| 3,034,403 | 5/1962 | Neefe . |
| 3,454,332 | 7/1969 | Siegel . |
| 4,435,856 | 3/1984 | L'Esperance . |
| 4,449,257 | 5/1984 | Koeniger . |
| 4,451,938 | 6/1984 | Kelman . |
| 4,601,722 | 7/1986 | Kelman . |
| 4,605,409 | 8/1986 | Kelman . |
| 4,676,791 | 6/1987 | Lemaster et al. . |
| 4,702,244 | 10/1987 | Mazzocco . |
| 4,743,254 | 5/1988 | Davenport . |
| 4,781,717 | 11/1988 | Grendahl . |
| 4,808,181 | 2/1989 | Kelman . |
| 5,002,571 | 3/1991 | O'Donnell, Jr. et al. . |
| 5,011,494 | 4/1991 | Von Recum et al. . |
| 5,076,684 | 12/1991 | Simpson et al. . |
| 5,089,023 | 2/1992 | Swanson . |
| 5,171,320 | 12/1992 | Nishi ........................................... 623/6 |
| 5,366,501 | 11/1994 | Langerman . |
| 5,370,687 | 12/1994 | Poler . |
| 5,405,385 | 4/1995 | Heimke et al. . |
| 5,549,670 | 8/1996 | Young et al. . |
| 5,674,283 | 10/1997 | Stoy . |

FOREIGN PATENT DOCUMENTS

| | | |
|---|---|---|
| 0246754 | 11/1987 | European Pat. Off. . |
| 0457553 | 11/1991 | European Pat. Off. . |
| 0458508 | 11/1991 | European Pat. Off. . |
| 507292 | 10/1992 | European Pat. Off. . |
| 599457 | 6/1994 | European Pat. Off. . |
| 1537244 | 1/1990 | U.S.S.R. . |
| 2181355 | 4/1987 | United Kingdom . |
| 8909576 | 10/1989 | WIPO . |
| 9300204 | 1/1993 | WIPO . |

OTHER PUBLICATIONS

Cataract Refractive Surg., vol. 18, pp. 333–341, Jul. 1992.
Experimental Cell Research 167 (1986) pp. 203–217.
Choyce, Rayner & Keeler Limited, Catalogue No. 469, 7/78.

*Primary Examiner*—David J. Isabella
*Attorney, Agent, or Firm*—Stout, Uxa, Buyan & Mullins, LLP; Frank J. Uxa

[57] ABSTRACT

An intraocular lens implantable in an eye includes an optic for placement in the capsular bag of the eye and for directing light toward the retina of the eye. The optic has a central optical axis, an anterior face, an opposing posterior face and a peripheral edge surface between the faces. The peripheral edge surface has a substantially continuous curved configuration in the direction between the faces. The intersection of the peripheral edge surface and at least one of the anterior face and the posterior face, preferably both of such faces, forms a peripheral corner located at a discontinuity between the peripheral edge surface and the intersecting face or faces. The present IOLs inhibit cell growth from the eye in front of or in back of the optic and reduce glare obtained in the eye in which the IOL is located.

28 Claims, 2 Drawing Sheets

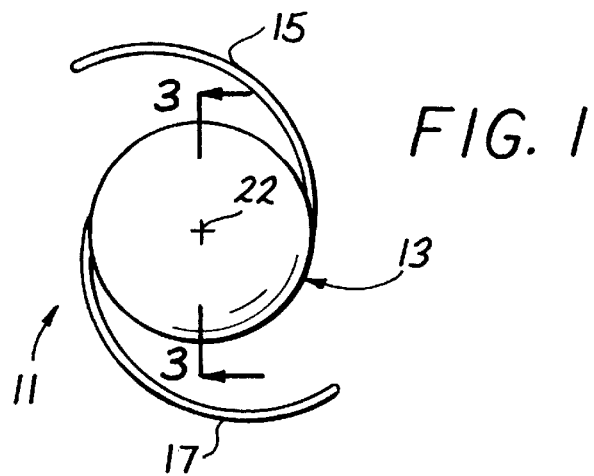
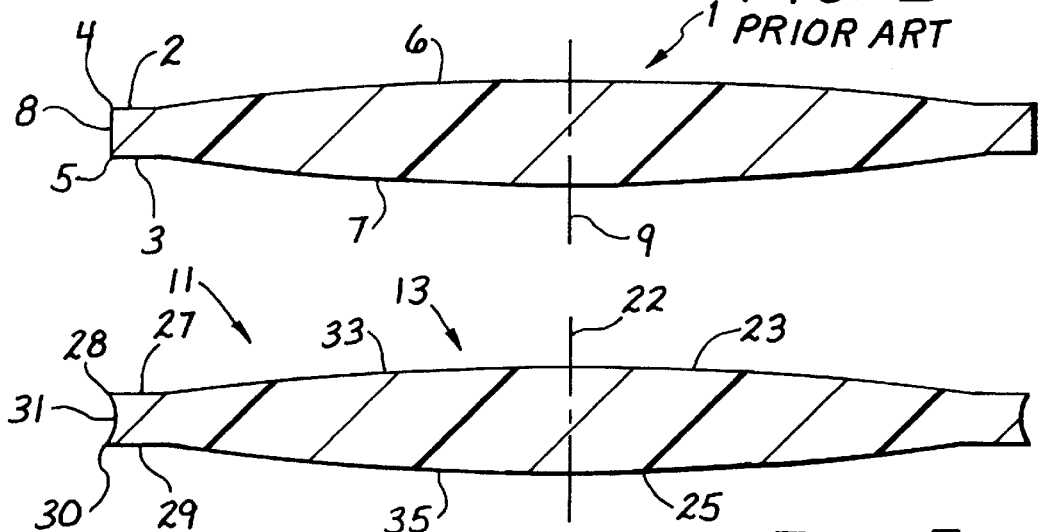
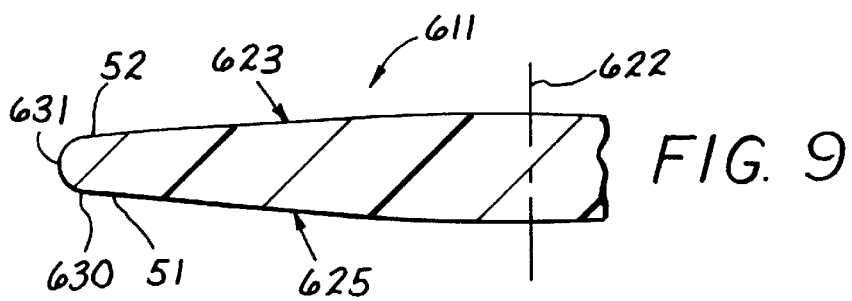
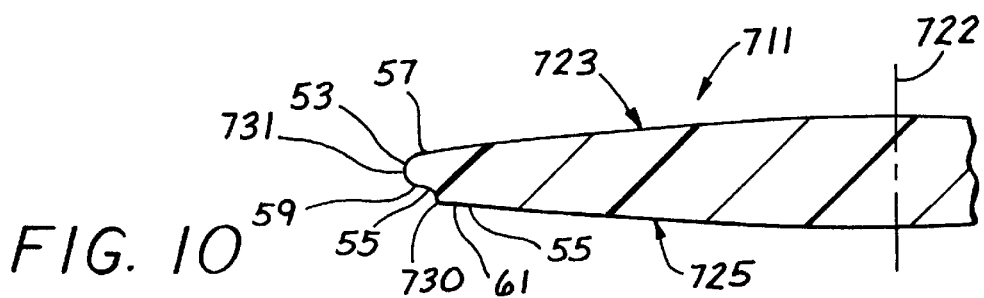

IOI FOR INHIBITING CELL GROWTH AND REDUCING GLARE

BACKGROUND OF THE INVENTION

This invention relates to intraocular lenses (IOLs) and, more particularly, to IOLs which inhibit migration or growth of cells from the eye onto the IOL and reduce glare in the eye.

An intraocular lens is commonly used to replace the natural lens of a human eye when warranted by medical conditions. It is common practice to implant an IOL in a region of the eye known as the capsular bag or posterior capsule.

One problem that is experienced with many IOLs following implantation is that cells from the eye, particularly epithelial cells from the capsular bag, tend to grow in front of and/or in back of the optic of the IOL. This tends to block the optic of the IOL and to impair vision.

A common treatment for this condition is to use a laser to destroy the cells and a central region of the capsular bag. Although this treatment is effective, the laser is expensive and is not available throughout the world. There is also cost associated with the laser treatment as well as some patient inconvenience and risk of complications. Finally, the laser treatment may affect the performance of some IOLs.

Another problem that is experienced after IOLs are implanted has to do with glare caused by light reflecting off of the IOLs, in particular, the edges of IOLs. Such glare can be an annoyance to the patient and may even lead to removal and replacement of the IOL.

It would be advantageous to provide IOLs which inhibit growth of cells from the eye onto the IOLs and which reduce glare caused by the IOLs in the eye.

SUMMARY OF THE INVENTION

New IOLs have been discovered. Such IOLs are effective to inhibit cell growth, in particular epithelial cell growth, onto the optic of the IOLs. In addition, the IOLs are structured so as to reduce glare, in particular edge glare, in the eye resulting from the presence of the IOL. The present IOLs are straightforward in design and construction, are easily manufactured, and are effective and produce substantial benefits in use in the eye.

In one broad aspect of the present invention, the present IOLs are implantable in the eye and comprise an optic having a central optical axis, an anterior face, an opposing posterior face and a peripheral edge between the faces. The optic is adapted for placement in the capsular bag of the eye and for directing light toward the retina of the eye. In a very useful embodiment, the IOLs further comprise at least one fixation member, and preferably two elongated fixation members, coupled to the optic for use in fixing the IOLs in the eye.

The peripheral edge of the present IOLs has a substantially continuous curved configuration in the direction between the anterior and posterior faces of the optic, that is between the faces in a cross-sectional plane including the optical axis. In the event that only a portion of the peripheral edge has the substantially continuous curved configuration, another portion, for example, the remaining portion, of the peripheral edge preferably has a straight line configuration in the direction between the anterior and posterior faces of the optic which is not parallel to the optical axis. More preferably, the entire peripheral edge has a substantially continuous curved configuration in the direction between the anterior and posterior faces of the optic. One or more of at least part of the peripheral edge, a portion of the anterior face near the peripheral edge surface and a portion of the posterior face near the peripheral edge surface is at least partially opaque to the transmission of light, which opacity is effective in reducing glare. Such opacity can be achieved in any suitable manner, for example, by physically roughening the selected portions of the optic. The present IOLs preferably provide reduced glare in the eye relative to the glare obtained with a substantially identical IOL having a peripheral edge surface parallel (flat) to the central optical axis in the direction between the faces of the optic.

In addition, the intersection of the peripheral edge surface and at least one, and preferably both, of the anterior face and the posterior face forms a peripheral corner edge located at a discontinuity between the peripheral edge surface and the intersecting face. Such peripheral corner edge, which may be considered a sharp, abrupt or angled peripheral corner edge, is effective in inhibiting migration or growth of cells from the eye onto the IOL. Preferably, the present IOLs, with one or two such angled peripheral corner edges, provide that cell growth from the eye in front of or in back of the optic is more inhibited relative to a substantially identical IOL without the sharp, abrupt or angled peripheral corner edge or corner edges.

The peripheral edge surface and the intersecting face or faces intersect at an angle or angles, preferably in a range of about 45° to about 135°, more preferably in a range of about 60° to about 120°. In one embodiment, an obtuse angle (that is greater than 90° and less than 180) of intersection is provided. Such angles of intersection are very effective in facilitating the inhibition of cell migration or growth onto and/or over the anterior face and/or posterior face of the optic of the present IOL.

In one very useful embodiment, at least one, and preferably both, of the anterior face and the posterior face has a peripheral region extending from the peripheral edge surface toward the central optical axis. The peripheral region or regions are substantially planar, preferably substantially perpendicular to the central optical axis.

In a very useful embodiment, the anterior face and the posterior face each has a peripheral region extending from the peripheral edge surface toward the central optical axis which is substantially planar, more preferably substantially perpendicular to the central optical axis. The peripheral regions preferably have a radial dimension of at least about 0.1 mm, and more preferably no greater than about 2 mm.

The dimension of the optic parallel to the central optical axis between the anterior face and the posterior face preferably is smaller at or near the peripheral edge surface, for example, at the peripheral region or regions, than at the central optical axis.

In one embodiment, at least a part or a portion of the peripheral edge surface of the optic is generally convex relative to the central optical axis. Alternately, at least a part or a portion of the peripheral edge surface of the optic is generally concave relative to the central optical axis. In a particularly useful embodiment, a first portion of the peripheral edge surface is generally convex relative to the central optical axis and a second portion of the peripheral edge surface is generally concave relative to the optical axis.

Preferably, the peripheral edge surface and/or the peripheral region or regions circumscribe the central optical axis. The anterior face and the posterior face preferably are both generally circular in configuration. At least one of the anterior and posterior faces has an additional region, located radially inwardly of the peripheral region, which is other than substantially planar.

Each and every combination of two or more features described herein is included within the scope of the present invention provided that such features are not mutually inconsistent.

The invention, together with additional features and advantages thereof, may best be understood by reference to the following description taken in connection with the accompanying illustrative drawings in which like parts bear like reference numerals.

BRIEF DESCRIPTION OF THE DRAWINGS

FIG. 1 is a plan view of one form of IOL constructed in accordance with the teachings of this invention.

FIG. 2 is a cross-sectional view of an optic of a prior art IOL.

FIG. 3 is a cross-sectional view taken generally along line 3—3 of FIG. 1.

FIG. 9 is a partial cross-sectional view of the optic of a still further embodiment of an IOL in accordance with the present invention.

FIG. 10 is a partial cross-sectional view of the optic of still another embodiment of an IOL in accordance with the present invention.

DESCRIPTION OF THE PREFERRED EMBODIMENTS

Figure 4:
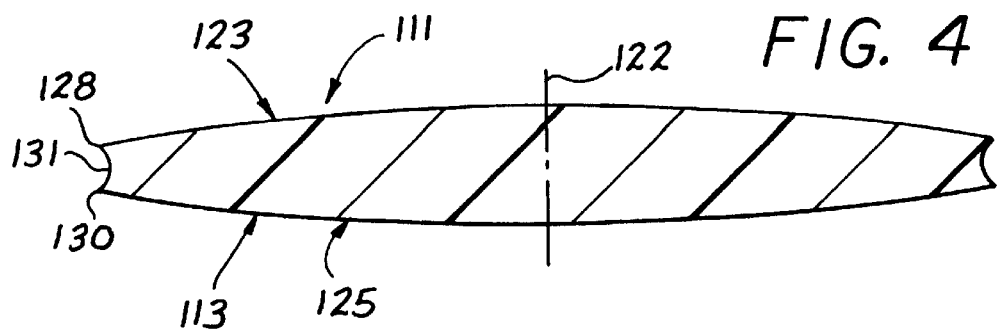
FIG. 4 is a cross-sectional view of the optic of an alternate embodiment of an IOL in accordance with the present invention.

FIG. 1 shows an IOL 11 which generally comprises an optic 13 and fixation members 15 and 17. In this embodiment, the optic 13 may be considered as effective for focusing light on or near the retina of the eye. Optical axis 22 passes through the center of optic 13 in a direction generally transverse to the plane of the optic.

In this embodiment, the optic 13 is circular in plan and bi-convex approaching the optical axis 22. However, this configuration is clearly illustrative as other configurations and shapes may be employed. The optic 13 may be constructed of any of the commonly employed materials used for rigid optics, such as polymethylmethacrylate (PMMA), or commonly employed materials used for resiliently deformable optics, such as silicone polymeric materials, acrylic polymeric materials, hydrogel-forming polymeric materials, mixtures thereof and the like.

The fixation members 15 and 17 in this embodiment are generally C-shaped and are integral with the optic 13. However, this is purely illustrative of the fixation members 15 and 17 as the fixation members may be of other configurations and/or may be separate members affixed to the optic 13 in any of a variety of conventional ways.

With particular reference to FIG. 3, the optic 13 has an anterior face 23, a posterior face 25, an anterior peripheral region 27, a posterior peripheral region 29 and a peripheral edge surface 31. The peripheral edge surface 31 has a continuously curved, concave configuration, for example, in cross-section. The peripheral edge surface 31 intersects anterior peripheral region 27 at anterior peripheral corner edge 28 at an angle of about 70°. Corner edge 28 is at a discontinuity between anterior face 23 (anterior peripheral region 27) and peripheral edge surface 31, and circumscribes optical axis 22. Peripheral edge surface 31 intersects posterior peripheral region 29 at posterior peripheral corner edge 30 at an angle of about 70°. Corner edge 30 is at a discontinuity between posterior face 25 (posterior peripheral region 29) and peripheral edge surface 31, and circumscribes optical axis 22.

The anterior and posterior peripheral regions 27 and 29 extend radially inwardly, for example, for a distance of about 0.1 mm to about 1.0 mm or more (about 0.5 mm as shown in FIG. 3), from the peripheral edge surface 31, and peripheral corner edge 28 and 30 respectively, and are substantially planar, more particularly, substantially perpendicular to the optical axis 22 of optic 13. Anterior face 23 includes an additional anterior region 33 which is convex, not planar. Posterior face 25 includes an additional posterior region 35 which also is convex, not planar. The dimension of optic 13 between anterior face 23 and posterior face 25 at the peripheral regions 27 and 29 is smaller than the same dimension at the optical axis 22.

It is found that implanting IOL 11 in the capsular bag of an eye effectively inhibits or retards cell migration or growth, for example, epithelial cell migration or growth, from the eye onto and/or over the anterior and posterior faces 23 and 25 of optic 13. In addition, it is found that a reduced amount of edge glare is obtained with the IOL 11 implanted in the capsular bag of the eye.

Without wishing to limit the invention to any particular theory of operation, it is believed that the present IOL 11 provides for inhibition of cell migration or growth onto and/or over the optic 13 because of the sharp or abrupt peripheral corner edges 28 and 30. Thus, it is believed that the cells from the eye have a reduced tendency to grow onto and/or over the anterior face 23 and posterior face 25 relative to a substantially identical IOL without such peripheral corner edge. In addition, it is believed that the reduced glare obtained using the present IOL 11 results from the curved configuration of the peripheral edge surface 31. Thus, IOL 11 including the substantially continuously curved peripheral edge surface 31 provides reduced glare relative to a substantially similar IOL having a peripheral edge surface which is substantially parallel, for example, in cross-section, to the optical axis of the IOL.

FIG. 2 illustrates a prior art IOL 1 which has planar peripheral regions 2 and 3 and sharp peripheral corner edges 4 and 5 on the anterior and posterior faces 6 and 7, respectively, but has a peripheral edge surface 8 which is parallel, rather than substantially continuously curved, to the optical axis 9. Although the prior art IOL 1 does provide some degree of inhibition of cell growth, it does not provide reduced edge glare as do the IOLs in accordance with the present invention.

FIG. 4 illustrates an alternate embodiment of an IOL in accordance with the present invention. This IOL is shown generally at 111. Except as expressly described herein, IOL 111 is structured and functions similarly to IOL 11. Components of IOL 111 which correspond to components of IOL 11 are indicated by the same reference numeral increased by 100.

The principal difference between IOL 111 and IOL 11 relates to the shape of the anterior face 123 and the shape of posterior face 125. Specifically, anterior face 123 is convex throughout, and IOL 111 does not include a substantially planar anterior peripheral region. This convex anterior face 123 intersects peripheral edge surface 131 at sharp anterior peripheral corner edge 128. Similarly, posterior face 125 is convex throughout, and IOL 111 does not include a substantially planar posterior peripheral region. This convex posterior face 125 intersects peripheral edge surface 131 at sharp posterior peripheral corner edge 130. The specific configuration of anterior face 123 and posterior face 125 can be independently provided to address the needs of any given specific application including the following factors; the vision correction or corrections desired, the size of optic 113, the size of the eye in which IOL 111 is to be placed and the like factors. IOL 111 inhibits or retards cell migration or growth and provides a reduced amount of edge glare as does IOL 11, described above.

Figure 5:
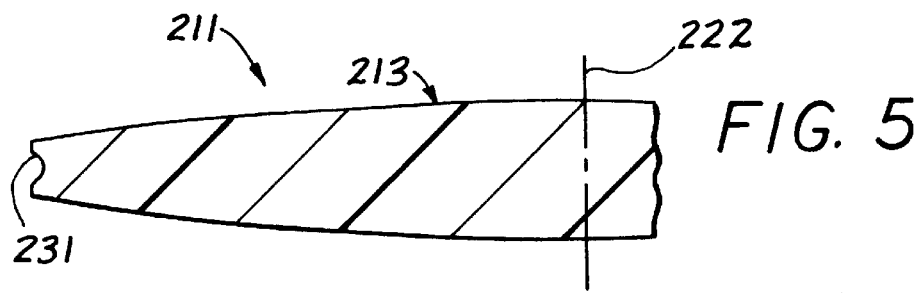
FIG. 5 is a partial cross-sectional view of the optic of a further embodiment of an IOL in accordance with the present invention.

FIG. 5 illustrates a further embodiment of an IOL in accordance with the present invention. This IOL is shown generally at 211. Except as expressly described herein, IOL 211 is structured and functions similarly to IOL 111. Components of IOL 211 which correspond to components of IOL 111 are indicated by the same reference numeral increased by 100.

The principal difference between IOL 211 and IOL 111 relates to the shape of peripheral edge surface 231. Specifically, the curvature of peripheral edge surface 231 is more complex relative to the curvature of peripheral edge surface 131. In particular, the curvature of edge surface 231 varies substantially continuously while the curvature of edge surface 131 is a substantially constant concave arc (in cross-section). Peripheral edge surface 231 is configured to reduce the amount of edge glare obtained with IOL 211 in the eye relative to, for example, IOL 1. The specific configuration or curvature of peripheral edge surface 231 is provided to address the needs of a specific application, including the following factors: the size of the optic 213, the size of the eye in which the IOL 111 is to be placed and the like factors.

Figure 6:
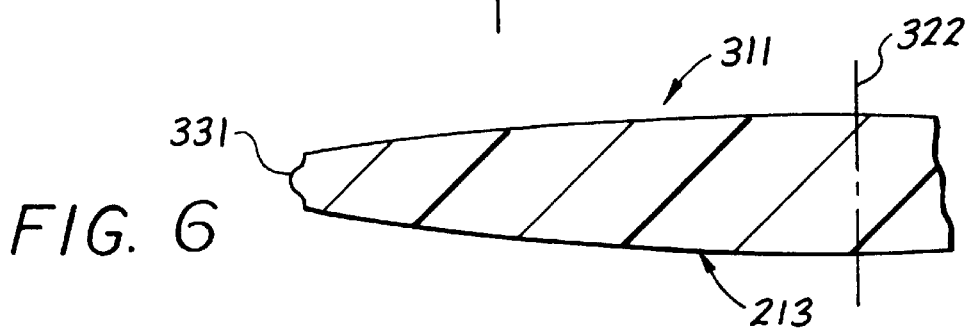
FIG. 6 is a partial cross-sectional view of an additional embodiment of an IOL in accordance with the present invention.

FIG. 6 illustrates an additional embodiment of the present invention. The IOL illustrated in FIG. 6 is shown generally at 211. Except as expressly described herein, IOL 211 is structured and functions similarly to IOL 111. Components of IOL 311 which correspond to components of IOL 111 are indicated by the same reference numeral increased by 200.

The primary difference between IOL 311 and IOL 111 relates to the configuration of peripheral edge surface 331. Specifically, the curvature of peripheral edge surface 331 varies substantially continuously (in a manner which is substantially the reverse of the curvature of peripheral edge surface 231 of IOL 211) while the curvature of edge surface 131 is a substantially constant concave arc (in cross-section). The peripheral edge surface 331 of IOL 311 is effective in reducing the glare caused by the presence of IOL 311 in the eye relative to the glare obtained with IOL 1 in the eye.

Figure 7:
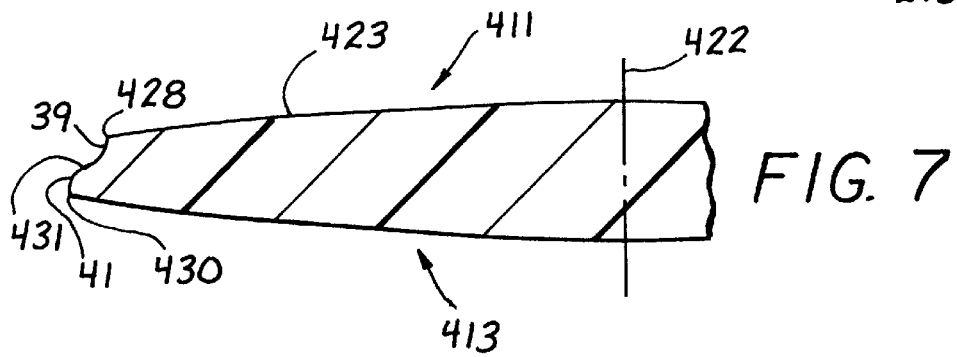
FIG. 7 is a partial cross-sectional view of the optic of another embodiment of an IOL in accordance with the present invention.

FIG. 7 illustrates an additional embodiment of an IOL in accordance with the present invention. Except as expressly described herein, this IOL, shown generally at 411 is structured and functions similarly to IOL 111. Components of IOL 411 which correspond to components of IOL 111 are indicated by the same reference numeral increased by 300.

The primary difference between IOL 411 and IOL 111 relates to the configuration of the peripheral edge surface 431. Specifically, peripheral edge surface 431 includes a first portion 39 which is concave relative to the optical axis 422 of IOL 411. Peripheral edge surface 431 also includes a second portion 41 which is convex relative to the optical axis 422 of IOL 411. Thus, the curvature of the peripheral edge surface of the present IOLs, for example, peripheral edge surface 431 of IOL 411, can be relatively complex. Peripheral edge surface 431 is effective to provide reduced glare in the eye relative to IOL 1. In addition, it should be noted that the peripheral edge surface 431 intersects anterior face 423 at anterior peripheral corner edge 428 at an angle of about 90°. Similarly, the peripheral edge surface 431 intersects posterior peripheral region 329 at posterior peripheral corner edge 330 at an angle of about 90°.

IOL 411, as with all of the IOLs in accordance with the present invention, is effective in inhibiting or retarding cell migration or growth from the eye onto or over the optic 413.

Figure 8:
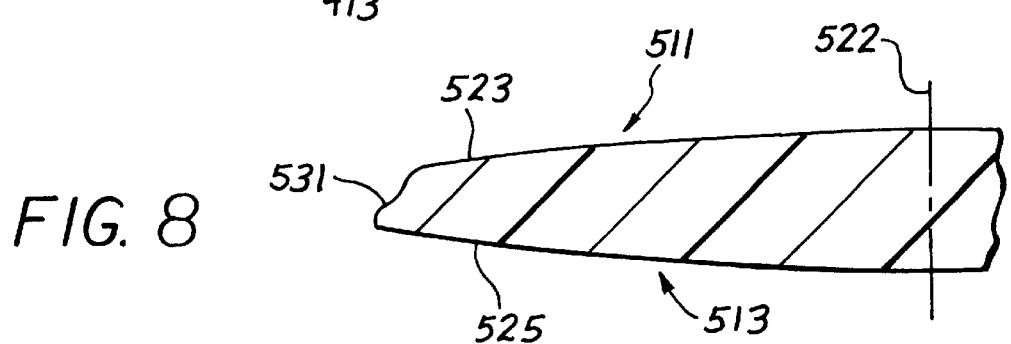
FIG. 8 is a partial cross-sectional view of the optic of a further alternate embodiment of an IOL in accordance with the present invention.

FIG. 8 illustrates a further alternate embodiment of an IOL in accordance with the present invention. This IOL is shown generally at 511. Except as expressly described herein, IOL 511 is structured and functions substantially similarly to IOL 111. Components of IOL 511 which correspond to components of IOL 111 are indicated by the same reference numeral increased by 400.

The primary differences between IOL 511 and IOL 111 relate to the configuration of peripheral edge surface 531 and the configuration of the intersection between anterior face 523 and peripheral edge surface 531 of optic 511. Specifically, peripheral edge surface 531 has a continuously curved configuration somewhat similar to peripheral edge surface 431 of IOL 411. Also, the anterior face 523 intersects peripheral edge surface 531 on a curve (that is on a continuity not at a discontinuity). In other words, the intersection of anterior face 523 and peripheral edge surface 531 is smooth or continuous, not sharp or discontinuous.

IOL 511 is effective in reducing the amount of glare obtained with IOL 511 in the eye relative to IOL 1 in the eye. Also, IOL 411 is effective in retarding or inhibiting migration from the eye onto and/or over cell growth or migration from the eye onto and/or over the posterior face 525 of IOL 511.

FIG. 9 illustrates a still further embodiment of an IOL in accordance with the present invention. Except as expressly described herein, this IOL, shown generally at 611 is structured and functions similarly to IOL 111. Components of IOL 611 which correspond to components of IOL 111 are indicated by the same reference numeral increased by 500.

The primary difference between IOL 611 and IOL 111 relates to the configuration of the peripheral edge surface 631 and to the configuration of posterior face 625. Specifically, peripheral edge surface 631 is convex relative to the optical axis 622 of IOL 611. Peripheral edge surface 631 does not intersect anterior face 623 at a sharp or discontinuous corner edge, but does intersect posterior face 625 at an obtuse angle at posterior peripheral corner 630. Posterior face 625 includes a peripheral region 51 which is substantially perpendicular to optical axis 622. Anterior face 623 includes a peripheral region 52 which is roughened so that region 52 is at least partially opaque to the transmission of light. The combination of the convex peripheral edge surface 631 and the at least partially opaque peripheral region 53 is particularly effective in reducing glare, for example, from corner 630, obtained with IOL 611 in the eye.

FIG. 10 illustrates still another embodiment of an IOL in accordance with the present invention. This IOL is shown generally at 711. Except as expressly described herein, IOL 711 is structured and functions substantially similarly to IOL 111. Components of IOL 711 which correspond to components of IOL 111 are indicated by the same reference numeral increased by 600.

The primary differences between IOL 711 and IOL 111 relate to the configuration of peripheral edge surface 731, the configuration of the intersection between anterior face 723 and peripheral edge surface 731 of optic 711 and the configuration of posterior face 725. Peripheral edge surface 731 includes a first portion 53 which is convex relative to optic axis 722 of IOL 711. Peripheral edge surface 731 also includes a second portion 55 which transitions from first portion 53 and intersects posterior 725 at corner 730. Peripheral edge surface 731 does not intersect anterior face 723 at a sharp or discontinuance corner edge. Posterior face 725 includes a peripheral region 55 which is substantially perpendicular to optical axis 722. Anterior face 723 includes the peripheral region 57 which is roughened so that region 57 is at least partially opaque to the transmission of light. Region 59 of peripheral edge surface 731 and region 61 of posterior face 725 are also roughened to be at least partially opaque to the transmission of light. The combination of the peripheral edge surface 731 and the at least partially opaque regions 57, 59 and 61 is particularly effective in reducing glare, for example, from corner edge 730, obtained with IOL 711 in the eye.

The present invention very effectively provides IOLs which inhibit cell growth or migration, in particular epithelial cell growth or migration from a capsular bag, onto and/or over the IOL optics. In addition, the IOLs produce reduced glare, in particular edge glare, relative to a lens having a peripheral edge surface which is substantially parallel, in cross-section, to the optical axis of the IOL optic. These benefits are achieved with IOLs which are easily manufactured and inserted in the eye. Such IOLs can be made of any suitable material, and provide effective performance and substantial benefits to the patient.

While this invention has been described with respect to various specific examples and embodiments, it is to be understood that the invention is not limited thereto and that it can be variously practiced within the scope of the following claims.

What is claimed is:

1. An intraocular lens implantable in an eye comprising:
   an optic adapted for placement in the capsular bag of the eye and for directing light toward a retina of the eye;
   the optic having a central optical axis, an anterior face including an anterior peripheral region, an opposing posterior face including a posterior peripheral region and at least one region which is other than substantially planar, and a peripheral edge surface between the faces;
   the peripheral edge surface not extending beyond the anterior peripheral region or the posterior peripheral region in a direction parallel to the central optical axis and having a substantially continuous curved configuration relative to the central optical axis in a direction between the faces parallel to the central optical axis; and
   the peripheral edge surface and the anterior face or the posterior face intersect to form a peripheral corner edge located at a discontinuity between the peripheral edge surface and the intersecting anterior or posterior face.

2. The intraocular lens of claim 1 wherein cell growth from the eye in front of or in back of the optic is more inhibited relative to a substantially identical intraocular lens without the peripheral corner edge.

3. The intraocular lens of claim 1 wherein the intersecting face is the posterior face.

4. The intraocular lens of claim 1 wherein the peripheral edge surface and the anterior face, and the peripheral edge surface and the posterior face each intersect to form a peripheral corner edge located at a discontinuity between the peripheral edge surface and the intersecting face.

5. The intraocular lens of claim 1 wherein the peripheral edge surface and the intersecting face intersect at an angle in a range of about 45° to about 135°.

6. The intraocular lens of claim 1 wherein the peripheral edge surface and the intersecting face intersect at an angle in a range of about 60° to about 120°.

7. The intraocular lens of claim 1 wherein the peripheral edge surface and the intersecting face intersect at an obtuse angle.

8. The intraocular lens of claim 1 wherein one or more of at least part of the peripheral edge surface, a portion of the anterior face near the peripheral edge surface and a portion of the posterior face near the peripheral edge surface is at least partially opaque.

9. The intraocular lens of claim 1 wherein reduced glare is obtained in the eye relative to a substantially identical intraocular lens having a peripheral edge surface parallel to the central optical axis.

10. The intraocular lens of claim 1 wherein at least part of the peripheral edge surface is generally convex relative to the central optical axis in a direction between the faces parallel to the central optical axis.

11. The intraocular lens of claim 1 wherein at least part of the peripheral edge surface is generally concave relative to the central optical axis in a direction between the faces parallel to the central optical axis.

12. The intraocular lens of claim 1 wherein a first portion of the peripheral edge surface is generally convex in a direction between the faces relative to the central optic axis and a second portion of the peripheral edge surface is generally concave relative to the central optical axis in a direction between the faces parallel to the central optical axis.

13. The intraocular lens of claim 1 wherein the peripheral edge surface circumscribes the central optical axis and the entire peripheral edge surface has a substantially continuous curved configuration relative to the central optical axis in a direction between the faces parallel to the central optical axis.

14. The intraocular lens of claim 1 wherein at least one of the anterior peripheral region and the posterior peripheral region extends from the peripheral edge surface toward the central optical axis and is substantially planar.

15. The intraocular lens of claim 14 wherein at least one of the anterior peripheral region and the posterior peripheral region is substantially perpendicular to the central optical axis.

16. The intraocular lens of claim 14 wherein both the anterior peripheral region and the posterior peripheral region extend from the peripheral edge surface toward the central optical axis and are substantially planar.

17. The intraocular lens of claim 1 which further comprises at least one elongated fixation member coupled to the optic for use in fixing the intraocular lens in the eye.

18. An intraocular lens implantable in an eye comprising:
   an optic adapted for placement in a capsular bag of an eye and for directing light toward a retina of the eye;
   the optic having a central optical axis, an anterior face including an anterior peripheral region, an opposing posterior face including a posterior peripheral region and at least one region which is other than substantially planar and a peripheral edge surface between the faces;

the peripheral edge surface not extending beyond the anterior peripheral region or the posterior peripheral region in a direction parallel to the central optical axis and having a substantially continuously curved configuration relative to the central optical axis in a direction between the faces parallel to the central optical axis;

the peripheral edge surface and the anterior face or the posterior face intersect to form a peripheral corner edge located at a discontinuity between the peripheral edge surface and the intersecting anterior or posterior face; and wherein cell growth from the eye in front of or in back of the optic is more inhibited relative to a substantially identical intraocular lens without the peripheral corner edge, and reduced glare is obtained in the eye relative to a substantially identical intraocular lens having a peripheral edge surface parallel to the optical axis.

19. The intraocular lens of claim 18 wherein the dimension of the optic parallel to the central optical axis between the anterior face and the posterior face is smaller at the peripheral edge surface than at the central optical axis.

20. The intraocular lens of claim 18 wherein both the anterior peripheral region and the posterior peripheral region extend from the peripheral edge surface toward the central optical axis and are substantially planar.

21. An intraocular lens implantable in an eye comprising:

an optic adapted for placement in a capsular bag of the eye and for directing light toward a retina of the eye;

the optic having a central optical axis, an anterior face including an anterior peripheral region, an opposing posterior face including a posterior peripheral region and at least one region which is other than substantially planar, and a peripheral edge surface between the faces;

the peripheral edge surface not extending beyond the anterior peripheral region or the posterior peripheral region in a direction parallel to the central optical axis; and the peripheral edge surface and the posterior face intersect to form a peripheral corner edge located at a discontinuity between the peripheral edge surface and the posterior face; and the intraocular lens being configured to provide reduced glare relative to a similar intraocular lens having an anterior peripheral region, a posterior peripheral region and a peripheral edge surface which are optically clear and a peripheral edge surface parallel to the central optical axis in a direction between the anterior and posterior faces of the optic.

22. The intraocular lens of claim 21 wherein the peripheral edge surface has a substantially continuous curved configuration relative to the central optical axis in a direction between the faces parallel to the central optical axis.

23. The intraocular lens of claim 21 wherein at least one of the anterior peripheral region, the posterior peripheral region and the peripheral edge surface is at least partially opaque.

24. The intraocular lens of claim 22 wherein at least one of the anterior peripheral region, the posterior peripheral region and the peripheral edge surface is at least partially opaque.

25. The intraocular lens of claim 21 wherein each of the anterior peripheral region, the posterior peripheral region and the peripheral edge surface is at least partially opaque.

26. The intraocular lens of claim 22 wherein each of the anterior peripheral region, the posterior peripheral region and the peripheral edge surface is at least partially opaque.

27. The intraocular lens of claim 21 wherein at least one of the anterior peripheral region, the posterior peripheral region and the peripheral edge surface is roughened.

28. The intraocular lens of claim 21 wherein each of the anterior peripheral region, the posterior peripheral region and the peripheral edge surface is roughened.

* * * * *